US012102550B2

United States Patent
De Lange et al.

(10) Patent No.: US 12,102,550 B2
(45) Date of Patent: Oct. 1, 2024

(54) BODY WEARABLE BRACE

(71) Applicant: STIL Group B.V., Delft (NL)

(72) Inventors: IJsbrand De Lange, Delft (NL); Stijn Jagers Op Akkerhuis, Wageningen (NL); Jonathan Cornel Van Den Hoorn, Delft (NL); Nicola Pambakian, Delft (NL); Hielke Jonathan De Jong, Dordrecht (NL)

(73) Assignee: STIL Group B.V., Delft (NL)

( * ) Notice: Subject to any disclaimer, the term of this patent is extended or adjusted under 35 U.S.C. 154(b) by 0 days.

(21) Appl. No.: 18/551,185

(22) PCT Filed: Mar. 29, 2022

(86) PCT No.: PCT/NL2022/050171
§ 371 (c)(1),
(2) Date: Sep. 18, 2023

(87) PCT Pub. No.: WO2022/211623
PCT Pub. Date: Oct. 6, 2022

(65) Prior Publication Data
US 2024/0164931 A1     May 23, 2024

(30) Foreign Application Priority Data

Mar. 29, 2021   (NL) ..................... 2027859

(51) Int. Cl.
*A61F 5/01*            (2006.01)
(52) U.S. Cl.
CPC ...... *A61F 5/013* (2013.01); *A61F 2005/0144* (2013.01); *A61F 2005/0155* (2013.01)
(58) Field of Classification Search
CPC .............. A61F 5/013; A61F 2005/0144; A61F 2005/0155; A61F 5/3715; A61F 5/3723;
(Continued)

(56) References Cited

U.S. PATENT DOCUMENTS

| 2,632,440 | A | * | 3/1953 | Hauser | ................ | A61F 5/0123 |
| | | | | | | 403/53 |
| 5,759,165 | A | * | 6/1998 | Malewicz | ............ | A61F 5/0125 |
| | | | | | | 602/21 |

(Continued)

OTHER PUBLICATIONS

International Search Report and Written Opinion received for PCT Patent Application No. PCT/NL2022/050171, dated Jun. 9, 2022, 13 pages.

(Continued)

*Primary Examiner* — Keri J Nelson
*Assistant Examiner* — Seth R. Brown
(74) *Attorney, Agent, or Firm* — AEON Law, PLLC; Adam L. K. Philipp; Charlotte E. Holoubek

(57) ABSTRACT

A body wearable brace, e.g. for resisting involuntary motion, adapted for allowing a user wearing the brace on his arm to dynamically move his or her upper arm, forearm, wrist and hand, comprising: an upper arm piece; a hand piece; an elbow flexion-extension joint that is rotatable relative to the upper arm piece around a first axis of rotation; a forearm pronation-supination joint that is rotatable relative to the forearm pronation-supination joint and the elbow flexion-extension joint around a second axis of rotation; an extension element extendable in a longitudinal direction; a wrist flexion-extension joint that is rotatable around a third axis of rotation. A first portion of the wrist flexion-extension joint is directly or indirectly connected to the extension element, and a second portion of the wrist flexion-extension joint is directly or indirectly connected to the hand piece.

20 Claims, 8 Drawing Sheets

(58) Field of Classification Search
CPC ..... A61F 5/373; A61F 5/3753; A61H 1/0274; A61H 1/0277; A61H 1/0285; A61H 2201/1635; A61H 2205/06; A61H 2205/065
See application file for complete search history.

(56) References Cited

U.S. PATENT DOCUMENTS

| | | | |
|---|---|---|---|
| 10,617,179 B2* | 4/2020 | Fiedler | A44B 11/12 |
| 2003/0223844 A1* | 12/2003 | Schiele | A63B 23/12 |
| | | | 414/5 |
| 2009/0030353 A1* | 1/2009 | Bonutti | A61H 1/0274 |
| | | | 601/5 |
| 2018/0235795 A1* | 8/2018 | Kuxhaus | A61F 5/013 |
| 2019/0201273 A1* | 7/2019 | Soltani-Zarrin | B25J 9/0006 |
| 2020/0009719 A1* | 1/2020 | Scattareggia Marchese | |
| | | | A61F 2/74 |
| 2020/0163787 A1* | 5/2020 | Goldfarb | A61F 5/013 |

OTHER PUBLICATIONS

Rocon et al., "Design and Validation of a Rehabilitation Robotic Exoskeleton for Tremor Assessment and Suppression" IEEE Transactions on Neural Systems and Rehabilitation Engineering, IEEE, USA, vol. 15, No. 3, Sep. 1, 2007 (Sep. 1, 2007), pp. 367-378.

* cited by examiner

BODY WEARABLE BRACE

RELATED APPLICATIONS

This application is a U.S. National Phase of PCT Patent Application No. PCT/NL2022/050171 having international filing date of Mar. 29, 2022, which claims the benefit of priority of Dutch Patent Application No. 2027859 filed on Mar. 29, 2022. The entire contents of the above-referenced applications and of all priority documents referenced in the Application Data Sheet filed herewith are hereby incorporated by reference for all purposes.

FIELD OF THE INVENTION

The present invention relates to a body wearable brace adapted for allowing a user wearing the brace on his arm to dynamically move his or her upper arm, forearm, and wrist, e.g. while reducing involuntary motion of the user's arm.

BACKGROUND ART

Spanish patent application ES 2 260 986 describes an orthotic for the control of forearm pronation and supination movement, which allows regulation of the relative rotational movement of the wrist with respect to the axis of the forearm. The known orthotic is adapted for suppressing involuntary movements, such as essential tremor, while still allowing the user to carry out voluntary movements over a wide range of motion. That is, the known device, like the present invention, allows dynamic movement of an arm of a user wearing the device, as opposed to braces which statically fix the position of a user's arm, e.g. to help the user to stretch but which do not allow a user the freedom of motion to perform activities of daily living.

The known orthotic comprises a main bar that is to be attached to a user at two points, one on the ulna near the olecranon, and one on the wrist by the ulnar side. At the point of attachment on the ulna near the olecranon rotational movement is allowed but longitudinal movement is not, and at the point of attachment to the wrist longitudinal movement of the main bar is allowed but rotational movement is not. To this end, the main bar has a top portion, that is used as linear guide, and a rounded bottom portion, the top portion running through a slide which does not allow rotation of the main bar, and wherein the bottom portion is inserted into a bearing with axial retention. The known orthotic is attached to the user by means of a wrist strip and a band located on the forearm, wherein the bar is connected via the slide to the wrist strip and to the band through a forearm support for the bearing support.

Though the known device may be useful to suppress involuntary movements of the forearm in patients with essential tremor, attaching the device to a user's wrist, forearm and upper arm may be difficult, especially for patients suffering from a tremor disorder.

It is an object of the invention to at least partially overcome this drawback.

SUMMARY OF THE INVENTION

To this end, the invention provides a body wearable brace adapted for allowing a user wearing the brace on his or her arm to dynamically move his or her upper arm, forearm, wrist and hand, the brace comprising: an upper arm piece, for connecting the brace to the user's upper arm; a hand piece, for connecting to the user's hand; an elbow flexion-extension joint, EFE joint, comprising a first portion fixed to the upper arm piece and comprising a second portion that is rotatable relative to the upper arm piece around a first axis of rotation, to allow flexion and extension of the elbow; a forearm pronation-supination joint, FPS joint, comprising a first portion fixed to the second portion of the EFE joint, and a second portion that is rotatable relative to the first portion of the FPS joint and the second portion of the EFE joint around a second axis of rotation, to allow pronation and supination of the forearm; an extension element extending in a longitudinal direction and comprising a first portion and a second portion which is moveable relative to the first portion along the longitudinal direction, wherein the first portion of the extension element is fixed to the second portion of the FPS joint; a wrist flexion-extension joint, WFE joint, comprising a first portion and a second portion that is rotatable relative to the first portion around a third axis of rotation to allow flexion and extension of the wrist, wherein the first portion of the WFE joint is directly or indirectly connected to the second portion of the extension element, and wherein the second portion of the WFE joint is directly or indirectly connected to the hand piece. In order to put on the device, the user may simply connect the upper arm piece to his or her upper arm and the hand piece to his or her hand; no straps or the like need to be connected to the user's forearm in order for the user to wear the brace.

The extension element, which may comprise one or more intermediate portions between the first and second portions, allows the brace to be put on and worn by a user without having to first manually adapt the brace to the length of the user's forearm. The extension element may further compensate for any misalignment between the user's elbow axis of rotation and first axis of rotation of EFE joint. In combination with the EFE, FPS and WFE joints, the extension element allows elbow flexion/extension, forearm pronation/supination as well as wrist flexion/extension while the brace still provides support for the user's hand. The brace thus provides at least three degrees of freedom of motion.

The brace may help to reduce involuntary motions during elbow flexion-extension, forearm pronation-supination, wrist adduction-abduction, WAA, and/or wrist flexion-extension, while allowing dynamic movement of the arm when the device is worn. The EFE, FPS, WAA, and WFE involuntary motions may respectively comprise EFE, FPS, WAA, and WFE tremors.

Tremor is a roughly sinusoidal involuntary vibration of a body part, occurring mostly in the upper extremities, which include the user's upper arm, forearm and wrist. Upper extremity tremor is mostly expressed as elbow flexion/extension tremor, forearm pronation/supination tremor, wrist abduction/adduction tremor and/or wrist flexion/extension tremor. The dominant tremor frequency varies between 3-7 Hz, whereas a higher frequency secondary component may be within the 8-12 Hz range. Though the tremor frequency generally does not vary substantially over time, e.g. varies only around ±0.5 Hz or less over 10 seconds, the amplitude of the tremor may vary considerably within short periods of time. The dominant frequency contains a substantial amount of the energy of the tremor, around 86%, and is the most obstructive in performing tasks, making the impact of higher harmonics negligible.

The second axis of rotation generally is at an angle of between 0 and 25 degrees, preferably between 5 and 15, degrees from an axis that is substantially normal to the first axis of rotation. The third axis of rotation generally is substantially normal to the second axis of rotation.

The brace is portable, i.e. can be worn by a user without requiring additional support such as stands or the like to hold the weight of the brace. The weight of the entire brace typically is less than 2 kg.

In an embodiment the brace is embodied such that no part of the brace, when worn, completely surrounds a portion of the user's forearm proximate to the elbow. In this manner, muscular expansion/retraction of the forearm does not affect how the brace is worn, and flow of blood through the forearm is not restricted by the brace.

In an embodiment the brace is adapted for being completely spaced apart from the user's forearm during use. In order to put on the brace, it thus suffices to attach the upper arm piece to the user's upper arm, and to attach the hand piece to the user's hand. As the user does not have to fit any part of the brace to her or his forearm, the brace can be relatively compact and/or light-weight, e.g. when compared to the brace described in ES 2 260 986. Moreover, by ensuring that the brace remains spaced apart from the forearm, it may be avoided that the brace applies pressure on sensitive areas such as the user's carpal tunnel.

In an embodiment, when worn, the upper arm piece extends over a length of at least one fourth of the length of the user's upper arm along the longitudinal direction of the upper arm. The brace is adapted for transferring force exerted by the hand, e.g. due to (involuntary) movement of the forearm or the hand, on the hand piece, via the extension element and the upper arm piece to the user's upper arm.

In an embodiment, when seen in projection onto a plane normal to the longitudinal direction, the third axis of rotation is spaced apart from the first portion of the extension element by a distance of at least 0.7 cm and preferably less than 7 cm, preferably between 2 and 5 cm. It may in this manner be prevented that when a user wearing the brace flexes her or his wrist, the flexion movement is blocked by contact of the user's wrist with the extension element or the WFE joint.

In a further embodiment, the WFE joint is a double joint comprising a pair of coupled joints. The mechanism prevents that the rotary joints rotate independently but only allow a linked movement of the joints. Accordingly, the linked movement enables the extension element to stay close to the arm of a user while the user's wrist in the handpiece flexes and extends.

In an embodiment, when seen in projection onto a plane parallel to and through the second axis of rotation, the longitudinal direction of the extension element is at an angle of between 0 and 30 degrees to the second axis of rotation, preferably at an angle of between 0 and 15 degrees, more preferably at an angle of between 5 and 12 degrees, e.g. 10 degrees. When the longitudinal direction is at a non-zero angle to the second axis of rotation, a shortest distance from the extension element to the hand piece is less than a shortest distance from the second axis of rotation to the hand piece, allowing the extension element to remain close to the user's forearm during use.

In an embodiment the first portion of the extension element is rotationally fixed to the first portion of the FPS joint, and rotation of the second portion of the extension element around an axis parallel to its longitudinal direction relative to the first portion of the WFE joint is substantially blocked. In this manner, involuntary motion, e.g. tremor, of the wrist and/or forearm can be reduced.

In an embodiment the hand piece is provided with a wrist adduction-abduction joint, WAA joint, comprising a first portion and a second portion that is rotatable relative to the first portion around a fourth axis of rotation, wherein the WAA joint is connected between the hand piece and the second portion of the extension element to allow adduction and abduction of the user's wrist. For instance, the WAA joint may allow both adduction and abduction over 45 degrees from a neutral position of the wrist. A first portion of the WAA joint may be fixed with respect to the second portion of the extension element, and a second portion of the WAA joint may be fixed with respect to the first portion of the WFE joint, so that the WAA joint interconnects the extension element and the WFE joint. Alternatively, a first portion of the WAA joint may be fixed with respect to the second portion of the WFE joint, and a second portion of the WAA joint may be fixed with respect to the hand piece, so that the WAA joint interconnects the WFE joint and the hand piece.

In an embodiment the EFE joint, WFE joint, the FPS joint and/or the WAA joint comprises a motion resisting element adapted for resisting rotation of the first portion of the joint relative to the second portion of the joint at a torque equal to or below a threshold. The motion resisting element typically allows its associated joint to rotate over its entire range of motion when a torque above the threshold is applied.

In an embodiment the EFE joint, WFE joint, the FPS joint and/or the WAA joint comprises a motion resisting element adapted for resisting fast rotation of the joint more than slower rotation of the joint. The motion resisting element, which typically allows its associated joint to rotate over its entire range of motion, may exert a greater resisting force on its joint if the first and second portion of the joint are rotated relative to each other at a higher speed than when they are rotated relative to each other at a lower speed. This allows high speed motions, e.g. tremors having a frequency of 2 Hz or more, to be dampened more effectively than voluntary motion.

In an embodiment the EFE joint, WFE joint, the FPS joint and/or the WAA joint is provided with a damper, such as fluid damper, liquid damper and/or a friction damper, for dampening rotation of the first portion of the joint relative to the second portion of the joint. The damper may be a motion resisting device as described with reference to the previous embodiment. If the EFE joint, WFE joint, FPS joint and/or the WAA joint includes a damper, then this respectively helps to absorb any EFE, WFE, FPS and/or WAA involuntary motion.

For instance, in case a friction damper is used, the friction damper may substantially block movement of the first portion of the joint relative to the second portion in case the torque between these two portions is equal to or below a predetermined threshold value, and otherwise allow the movement. In case a fluid or liquid damper is used, the damper may have a damping coefficient for dampening faster motions to a greater extent than slower motions.

In the table below examples are provided of suitable ranges of threshold values for each of these joints are given in case the joint is provided with a friction damper and in case the joint is provided with a fluid or liquid damper:

| Joint | Friction damper:<br>Example torque<br>threshold range | Fluid or liquid damper:<br>Example damping coefficient<br>range at 2 rad/s |
| --- | --- | --- |
| EFE | 0.1 . . . 2 Nm | 0.05 . . . 1 Nm/(rad/s) |
| FPS | 0.1 . . . 1 Nm,<br>preferably 0.5 Nm | 0.05 . . . 0.5 Nm/(rad/s) |

-continued

| Joint | Friction damper: Example torque threshold range | Fluid or liquid damper: Example damping coefficient range at 2 rad/s |
|---|---|---|
| WAA | 0.05 . . . 0.3 Nm | 0.02 . . . 0.2 Nm/(rad/s) |
| WFE | 0.1 . . . 0.6 Nm, preferably 0.2 Nm | 0.05 . . . 0.5 Nm/(rad/s), preferably 0.4 Nm/(rad/s) |

In an embodiment, the extension element is provided with a motion resisting element adapted for resisting translational motion of its first portion relative to its second portion. In case the extension element is provided with a friction damper, then the force threshold that is to be exerted along the longitudinal direction between the first and second portion in order to move these relative to each other is in the range of 5 to 30 N. In case the extension element is provided with a fluid or liquid damper, the damper coefficient thereof preferably lies in the range of 100 . . . 600 N/(m/s), at 0.05 m/s. The motion resisting element typically allows its first and second portion of the extension element to translate along the longitudinal direction over its entire range of motion.

In an embodiment the EFE joint, WFE joint, the FPS joint and/or the WAA joint are unbiased. That is, the joint or joints do not urge the elbow, forearm and/or wrist towards a fixed position. This may for instance be achieved by ensuring that the motion resisting element(s) or damper(s) are unbiased as well.

In an embodiment the first portion of the extension element is moveable relative to the second portion of the extension element along the longitudinal direction over a distance of at least 2 cm, preferably a distance of between 2 to 30 cm, more preferably a distance of between 4 to 18 cm.

In an embodiment the extension element is provided with one or more bearings, such as roller bearings and/or a low friction bearing, such as polytetrafluoroethylene, for allowing smooth sliding of the second portion relative to the first portion. For instance, the extension element may be formed as a slide rail comprising a low-friction plastic guide carriage element in a guide rail.

In an embodiment the extension element comprises a first member, such as a beam, comprising the first portion of the extension element, and a second member such as a beam, comprising the second portion of the extension element, wherein the second member is substantially freely slidable relative to the first beam along the longitudinal direction, preferably wherein the second member is rotationally fixed with respect to the first beam. The extension member may comprise one or more intermediate members, such as beams, between the first and second member.

In an embodiment the brace is adapted for allowing substantially free pronation and supination of the user's forearm over a range of at least 90 degrees pronation of the user's forearm to at least 90 degrees supination of the user's forearm, and/or for allowing substantially free flexion and extension of the user's wrist over a range of at least 45 degrees flexion of the user's wrist to at least 60 degrees extension of the user's wrist, when worn by the user. When there is no supination or pronation of the user's forearm, the forearm is defined to be in a neutral position with respect to supination and pronation, and when there is no flexion or extension of the user's wrist, the wrist is defined to be in a neutral position with respect to flexion and extension. The dynamic movement allowed by the brace includes substantially free pronation and supination of the user's forearm, and substantially free flexion and extension of the user's wrist. Preferably, the brace does not limit the extent to which the user's elbow can flex/extend when the user wears the brace, so that the brace also allows substantially free flexion/extension of the user's elbow.

In an embodiment the upper arm piece, the EFE joint, the FPS joint, the extension element, the WFE joint, the WAA joint, and/or the hand piece are configurable to be used on a user's right arm and left arm. In this manner, the same component or components can be used to construct a brace for left-handed use, and a brace for right-handed use. Typically, one or more of the components will have at least one plane of symmetry to achieve this.

In an embodiment the upper arm piece is provided with a first attachment element and with a second attachment element spaced apart from the first attachment element, wherein the first portion of the EFE joint is attached to the upper arm piece by means of either the first or the second attachment. Typically, when the upper arm piece has a plane of symmetry, the first and second attachment element will be located on different sides of said plane.

In an embodiment the upper arm piece comprises a shell adapted for, during use, being arranged at the triceps side of the user's upper arm, and wherein the shell is open ended at the biceps side of the user's upper arm to allow insertion of the user's upper arm from the open end. The shell thus does not prevent contraction or relaxation of the user's biceps. The shell typically has a substantially U-shaped cross section, to allow the shell to be placed partially around the user's upper arm. The U-shaped shell braces against the upper arm and may provide support for the extension element to reduce FSP tremor.

The upper arm piece may further be provided with an upper arm strap adapted for placement around a portion of the user's arm above the crook of the arm and below or at a lower side of the user's biceps, and for connecting to the shell. The strap and shell together are adapted for holding the upper arm piece in place with respect to the user's upper arm. Preferably, the upper arm piece further comprises a magnetic clasp for holding a portion of the upper arm strap in place with respect to the shell. A suitable magnetic clasp is described in U.S. Pat. No. 10,617,179 B2 which is incorporated herein by reference in its entirety. When the strap is placed around the user's arm and the clasp is closed, the strap will hold the upper arm piece in place with respect to the upper arm. When the strap is loose and the clasp is open, the user can easily place her or his upper arm in the upper arm piece.

In an embodiment the shell of upper arm piece comprises a substantially rigid material which is sufficiently rigid to allow the shell to maintain it shape during wear by the user. For instance, the shell of the upper arm piece may comprise a rigid plastic material.

In an embodiment the hand piece comprises either:
  a shell comprising a substantially rigid portion adapted for supporting the ulnar side and dorsal side of the user's hand during use while being spaced apart from the radial side of the user's hand; or
  a shell comprising a substantially rigid portion adapted for supporting the radial side and dorsal side of the user's hand during use while being spaced apart from the ulnar side of the user's hand; or
  a shell comprising a substantially rigid portion adapted for supporting either the radial side or the dorsal side of the user's hand during use while being spaced apart from the ulnar side of the user's hand.

In each case the shell has an open end, so that, once the user has put on the upper arm piece, he or she can easily place his or her hand in the shell via the open end, by bending the elbow. The substantially rigid portion ensures that, when a hand is placed in the hand piece during regular wear, the hand is supported by said rigid portion.

The hand piece may further be provided with one or more straps, such as a wrist strap and/or a palm strap, respectively for placement around the user's wrist or palm and connecting to the shell. Preferably, the hand piece comprises one or more magnetic clasps, e.g. as described in U.S. Pat. No. 10,617,179 B2, for holding a portion of the one or more straps in place with respect to the substantially rigid portion of the shell.

In an embodiment the hand piece consists of a rigid element configured to receive the dorsal side of user's hand, with straps to keep the rigid element in this position on the hand.

In an embodiment the substantially rigid portion of shell of the hand piece comprises a deformable metal sheet, for allowing the shape of hand piece to be adjusted to the user's hand. Though during regular wear, the rigid portion will substantially not deform, it is possible to fit the shell to the user's hand. Preferably, the shell further comprises one or more layers of plastic, e.g. a laminated stack of plastics covering the metal sheet, with optionally a layer of fabric and/or foam, on top the inner side of the plastic layer. The fabric and/or foam layers are detachably mounted on the hand piece, so that these can be washed separately.

In an embodiment the brace is completely passive. Thus, no electronically, hydraulically or pneumatically actively driven actuators or other electrical components are provided on the device for driving rotation of parts of the device around the first, second, third and/or fourth axis of rotation. The passive device can be constructed in a simple and cost-effective manner, and may be used without requiring the user to carry an external power supply. The weight of the entire passive brace typically is less than 1 kg, e.g. less than 0.5 kg.

In an embodiment the brace is provided with one or more sensors for sensing a relative position of one part of the brace to another part of the brace, and/or torque applied between one part of the brace and another part of the brace. For instance, the sensors may sense a relative position of the first portion to the second portion of the joint EFE joint, the FPS joint, the WFE joint, and/or the WAA joint. The extension element may be provided with a sensor for sensing a relative position of its first portion and the second portion. Examples of a suitable sensor for the EFE, FPS, WAA and WFE joints include a rotary encoder, for detecting angle and/or speed of rotation between the two portions of these joints, a torque sensor, for measuring torque between two portions of these joints. Inertia measurement units (IMUs) may be provided on the brace, e.g. on the shell of the upper arm piece and/or on the shell of the hand piece. For instance, each of the EFE joint, the FPS joint, the extension element the WAA joint, and/or the WFE joint may be provided with i) a sensor for sensing a relative position of the first part and the second part of the joint, ii) a sensor that measures torque between to the first part and the second part of the joint, and/or iii) a sensor that measures absolute acceleration or absolute angular velocity of the hand piece and/or upper arm piece.

Sensor data obtained from the sensors in this embodiment may be used to analyse a user's movement patterns. For instance, one or more of the EFE joint, FPS joint, WAA joint and the WFE joint may be provided with a rotary encoder for detecting an angle of rotation respectively of the first portion of the EFE joint around the first axis of rotation relative to the second portion of the EFE joint, of the first portion of the FPS joint around the second axis of rotation relative to the second portion of the FPS joint, of the first portion of the WAA joint around the second axis of rotation relative to the second portion of the WAA joint and of the first portion of the WFE joint around the third axis of rotation relative to the second portion of the WFE joint.

In an embodiment the EFE joint, the FPS joint, the WAA joint, the WFE joint and/or the extension element is provided with an actuator for urging the first portion and the second portion thereof of the joint to an adjustable position while the brace is worn by the user. Suitable actuators include electronically, hydraulically or pneumatically powered actuators, e.g. electromotors, piezo elements, as known to the skilled person. The actuators may be used to let a user wearing the device experience a simulated tremor, and/or to set a degree of motion dampening provided by the joints. When the brace is also provided with sensors as described above, the actuators may be used to counteract a portion of involuntary motion sensed by the sensors or generate desired motion for rehabilitation of stroke patients.

In an embodiment, the extension element is provided with a linear actuator, for driving linear movement between the first and second portion of the extension element.

In an embodiment the EFE joint, the FPS joint, the WAA joint, the WFE joint and/or the extension element is provided with an actuator for restricting involuntary motion while allowing voluntary motion. In addition to the electronically, hydraulically or pneumatically powered actuators described above, suitable actuators include electronically, hydraulically or pneumatically powered motors, dampers, brakes and/or clutches which can restrict motion, but may not be able urge movement to drive extension/flexion of the user's elbow, pronation/supination of the user's forearm, extension/flexion of the user's wrist and/or adduction/abduction of the wrist. The actuator may be adapted for resisting rotation of the first portion of the joint relative to the second portion of the joint at an angular velocity equal to or above a threshold value more than rotation of the first portion of the joint relative to the second portion of the joint at an angular velocity below the threshold value. For instance, the threshold may be set at an angular velocity of about 12.6 rad/s, which would dampen tremors of 2 Hz and greater more than lower frequency movements. Preferably one or more sensors as described herein are provided on the brace to be able to obtain a measure of whether a movement is voluntary or involuntary.

In an embodiment the brace comprises the EFE joint, the FPS joint, the extension element, the WFE joint and the hand piece, in which the FPS joint has a first portion integrated the housing of the EFE joint and a second portion that is configured to rotate around the second axis of rotation R2 with respect to the first portion. The second portion of the FPS joint is integrated in the extension element. The brace further comprises an axle extending between the first portion of the FPS joint and the second portion, along which axle the extension element can be moved to allow adjustment of the length of the brace.

SHORT DESCRIPTION OF DRAWINGS

The present invention will be discussed in more detail below, with reference to the attached drawings, in which like reference numerals refer to like structures and wherein:

FIGS. 1A and 1B show an isometric view of a brace according to a first embodiment, respectively with its straps in an open position allowing a user to put it on, and with its straps closed to attach the brace to the user;

FIGS. 1C and 1D respectively show an exploded view of the brace of FIG. 1A, and an exploded back view of the same brace with the straps removed;

FIG. 2A shows a detail of cross-sectional side along plane P of FIG. 1C;

FIG. 2B a detail of the brace of FIG. 1A, wherein the first portion of the FPS joint is in a rotated position relative to the second portion of said joint;

Figure 5A:
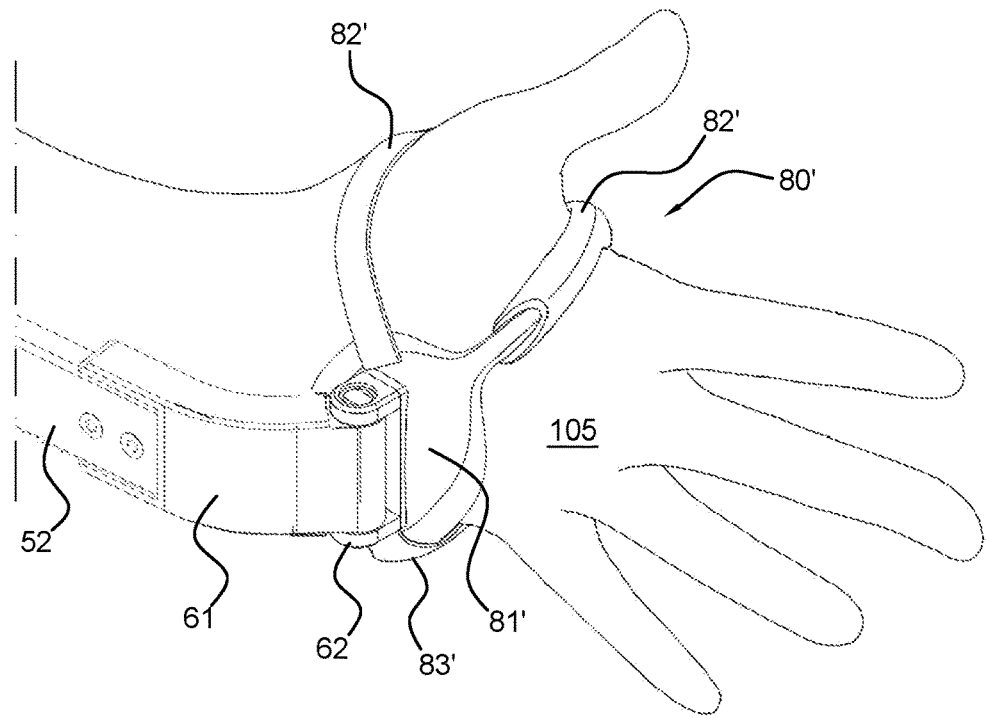
Figure 5B:
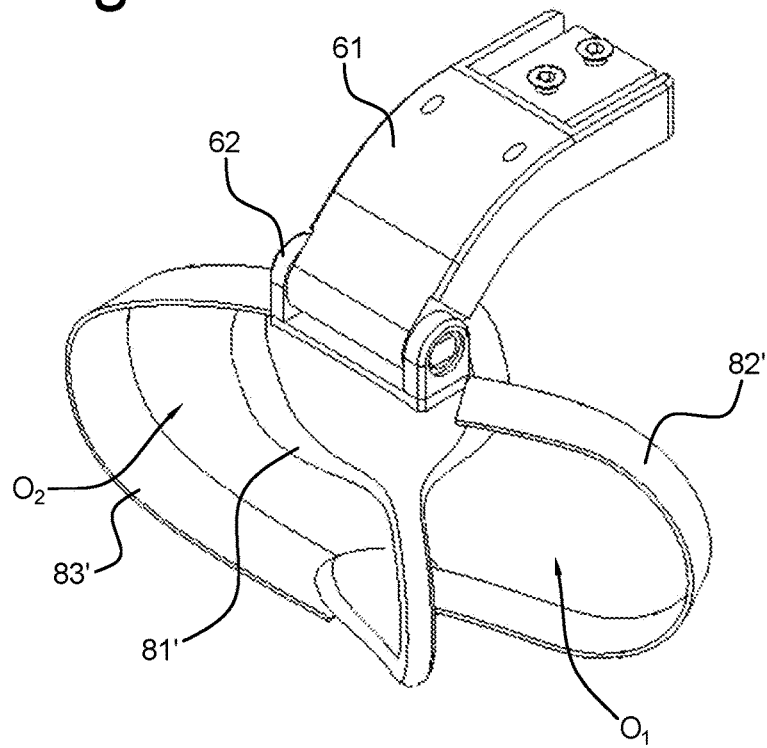
Figure 6A:
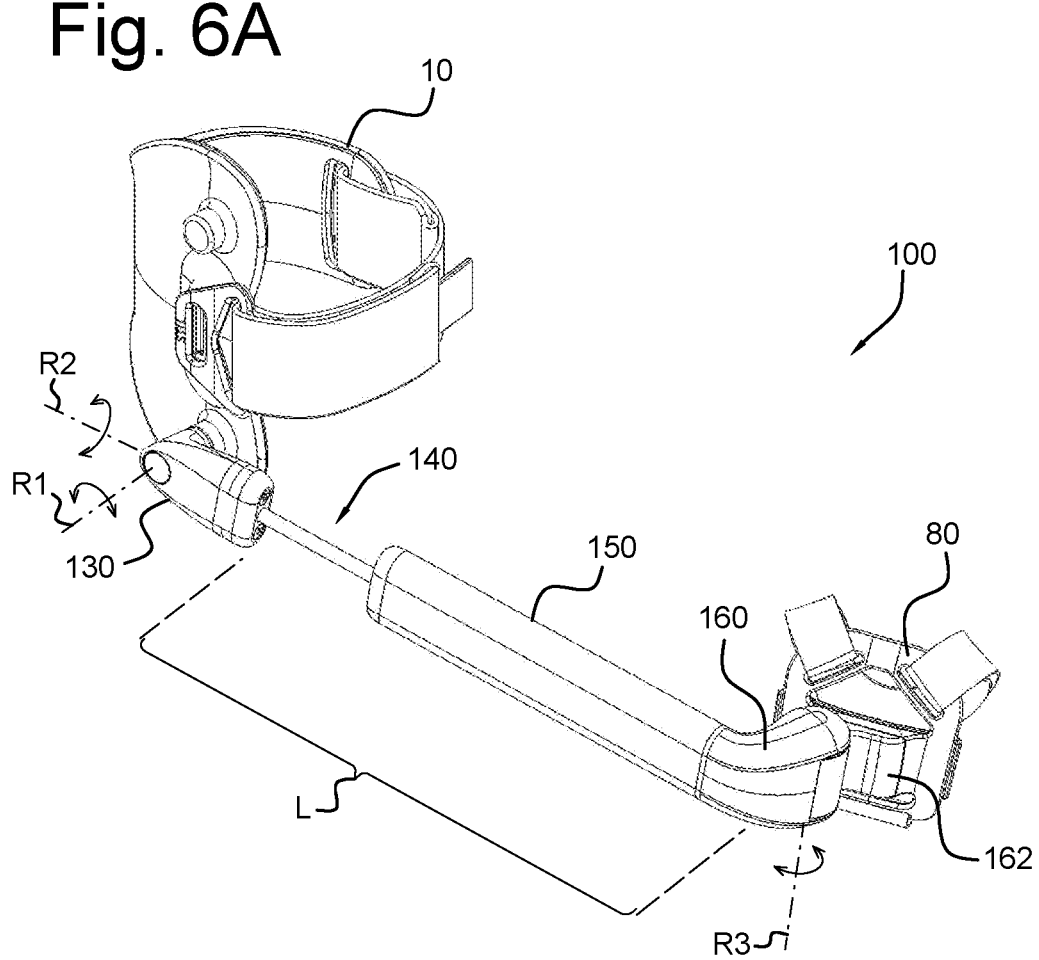
Figure 6B:
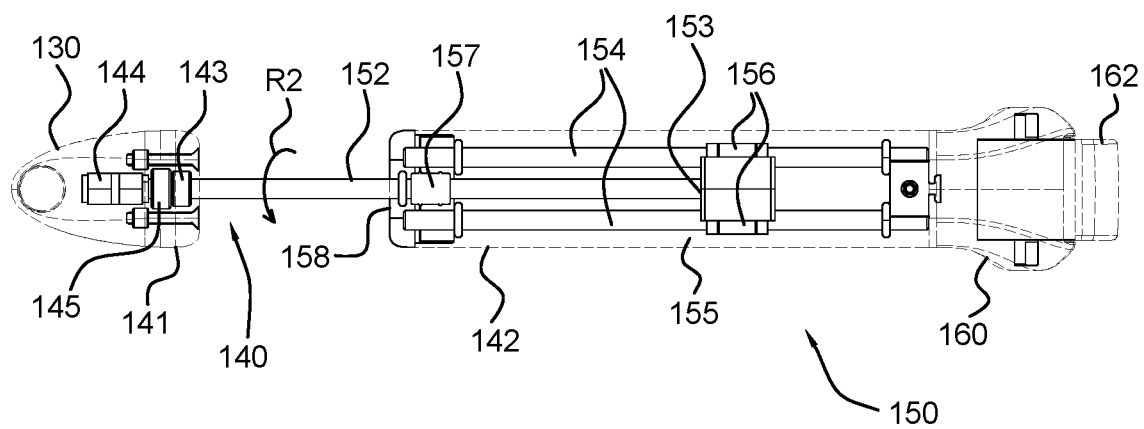
Figure 7:
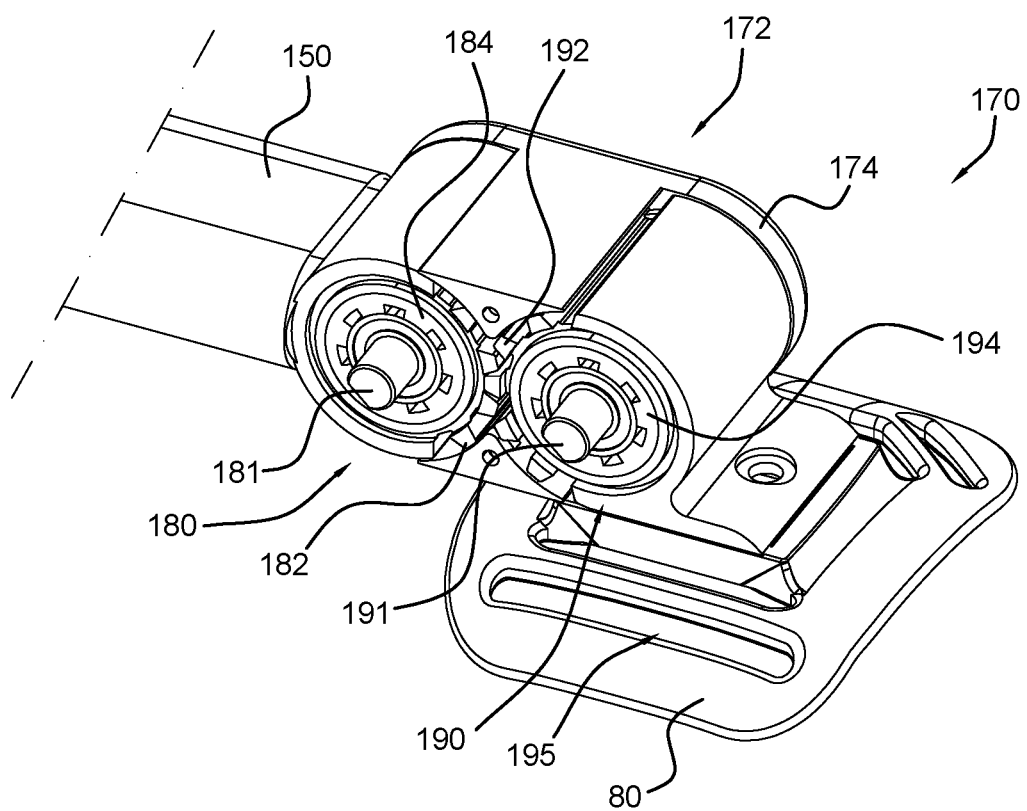

FIGS. 5A and 5B respectively show an alternative hand piece according to the invention as worn by a user, and a detail thereof;

FIGS. 6A and 6B show an isometric view of a brace according to an embodiment and an extension element as applied in the brace in a cutaway view; and FIG. 7 shows a cutaway view of an alternative mechanism for a wrist flexion-extension joint according to an embodiment.

DESCRIPTION OF EMBODIMENTS

Figure 1A:
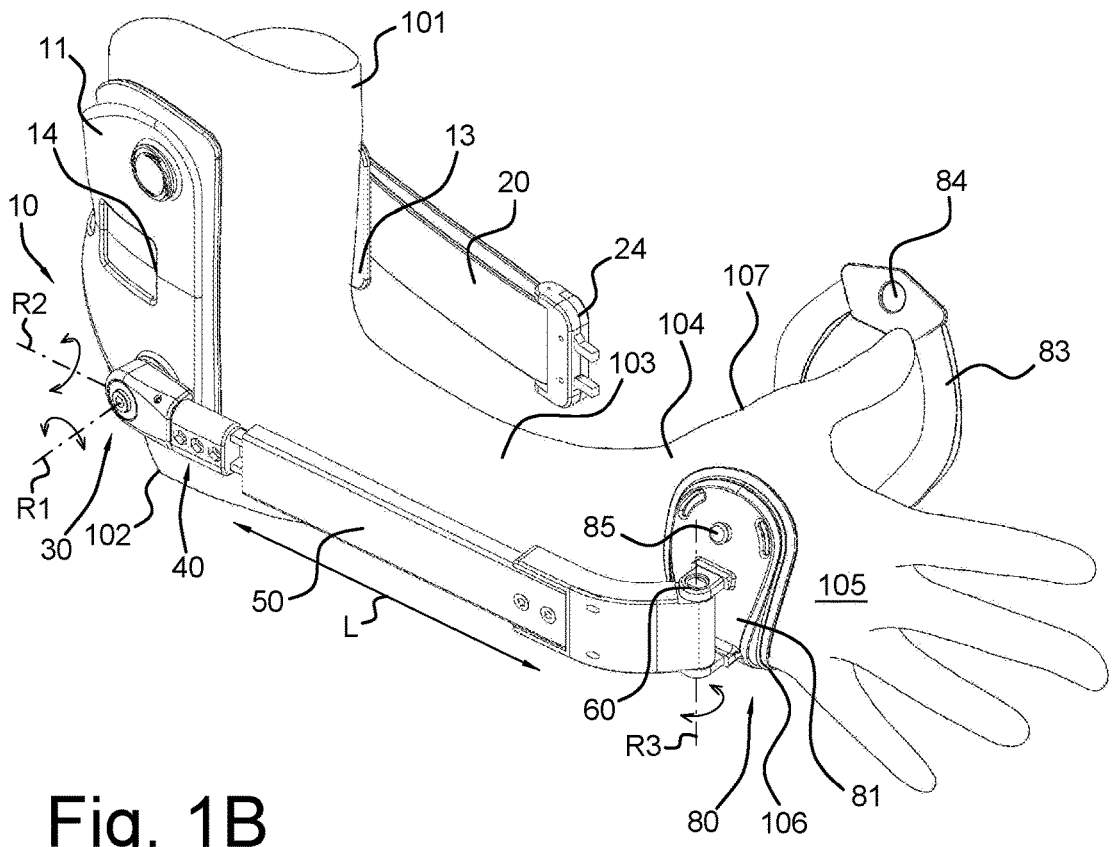
Figure 1B:
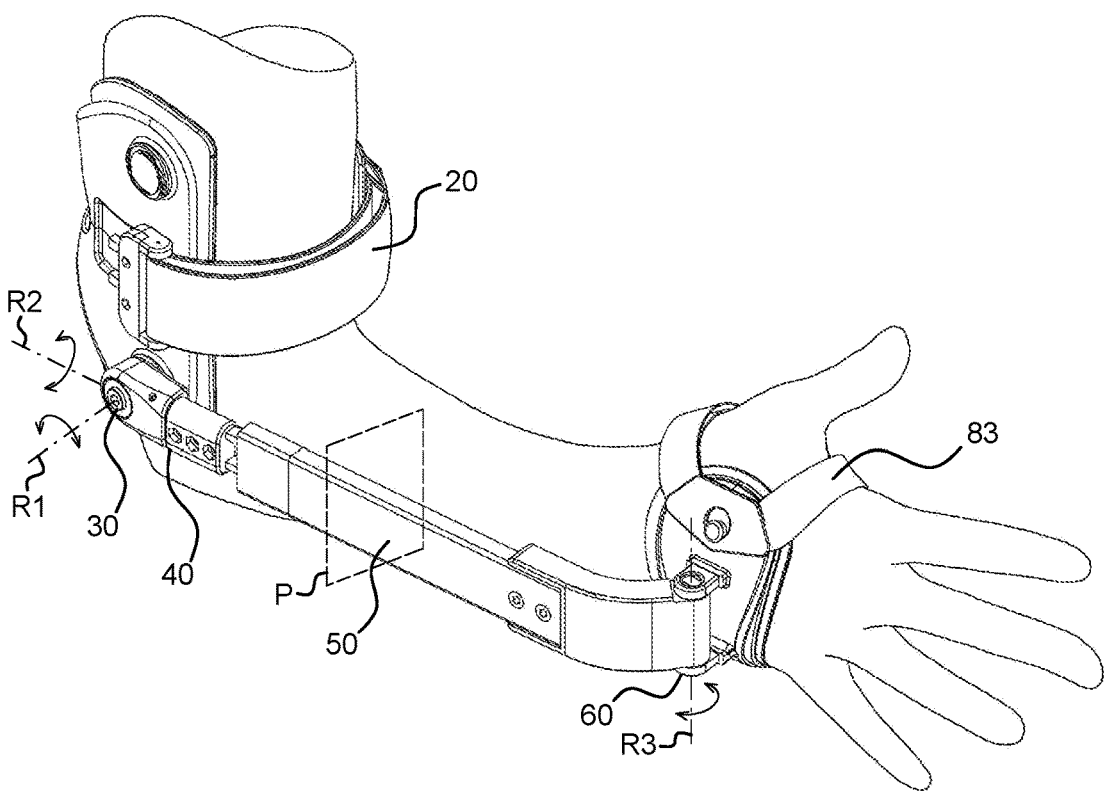

FIG. 1A shows a brace 1 according to the invention with open straps 20, 83, so that a user can put on the brace, and FIG. 1B shows the same brace worn on a user's right arm with closed straps. The brace comprises an upper arm piece 10 with a substantially rigid shell 11 with soft fabric or foam 13 on an inner side. The upper arm piece is to be worn on the user's upper arm 101, just above the elbow 102. Upper arm strap 20, which is provided for holding the upper arm piece in place with respect to the user's upper arm, comprises a magnetic clasp 24 which interlocks with a clasp-holder 14 that comprises a ferri- or ferromagnetic material and is provided on the shell 11. The shell 11 has a substantially a U-shaped cross section, allowing the shell 11 to be fitted partially around the user's upper arm 101 when the clasp 24 is undone and the upper arm strap 20 has been moved to away from the clasp-holder 14 and to the side. Once the shell 11 has been fitted in this way, the user can position the clasp 24 near the clasp holder 14, upon which the magnetic clasp 24 will auto-align itself with the holder 14 and interlock therewith, as shown in FIG. 1B.

The brace 1 further comprises a hand piece 80 with a shell 81, the shell comprising a substantially rigid plastic portion 81a for providing structural rigidity to support the user's hand on its dorsal side 105 and on its ulnar side 106, an intermediate deformable metal layer 81b that can be shaped to some extent to the shape of the user's hand, and a and a soft fabric or foam 81c on the inner side for contacting the user's hand. On a radial side 107 of the user's hand the shell 81 is open ended, allowing the user to easily place his or her hand in the shell 81. A flexible wrist and palm strap 83, shown in FIG. 1A in an open position, can be closed as shown in FIG. 1B, with the strap 83 having an opening for the user's thumb to pass through. The strap 83 comprises a magnetic clasp 84a for auto aligning and interlocking with metal stud 84b on the shell 81.

As shown in FIG. 1B, when the straps are closed, the shell 81 contacts the dorsal and ulnar side of a user's hand while remaining spaced apart from the radial side of the hand.

Attached to the upper arm piece 10 is an elbow flexion-extension, EFE, joint 30 which allows the user's elbow to flex or extend around first axis of rotation R1. A forearm pronation-supination, FPS, joint 40 is connected to the EFE joint 30, and allows pronation or supination of the forearm 103 around second axis of rotation R2. Connected to the FPS joint 40 is a first portion 51 of extension element 50, which is adapted for extending or retracting along its longitudinal direction L, which typically runs substantially along the longitudinal direction of the user's forearm during use. As the extension element can extend or retract based on movement of the user's arm, the length of the element 50 will easily adapt to a length suitable for the user when the user has put on the upper arm piece and the hand piece. The extension element 50 also improves the degree to which the user can freely flex or extent his or her wrist, as such movement typically changes the distance from the hand piece 80 to the FPS joint 40. In order to allow flexion and extension of the user's wrist, a wrist flexion-extension, WFE, joint 60 is attached to a second portion 52 of the extension element. The WFE joint allows the hand piece 80 to rotate around a third axis of rotation R3, relative to the extension element 50. In the example shown, the first portion 61 of the WFE joint is translationally and rotationally fixed with respect to the second end 52 of the extension element 50, i.e. the first portion 61 of the WFE joint is directly attached to the second end 52 of the extension element 50. The second portion 62 of the WFE joint 60 is translationally and rotationally fixed with respect to the rigid shell 81 of the hand piece 80, i.e. the second portion 62 is directly connected to the hand piece 80.

Figure 1C:
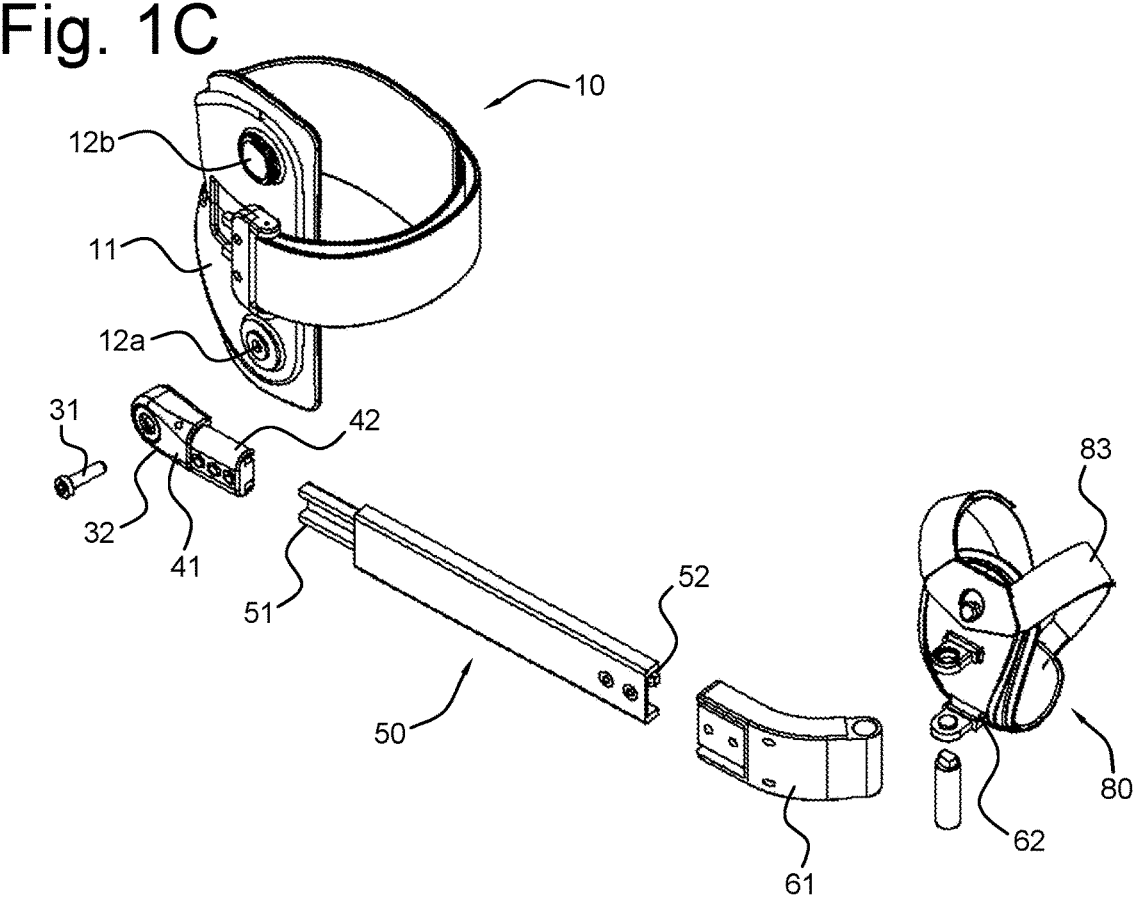
Figure 1D:
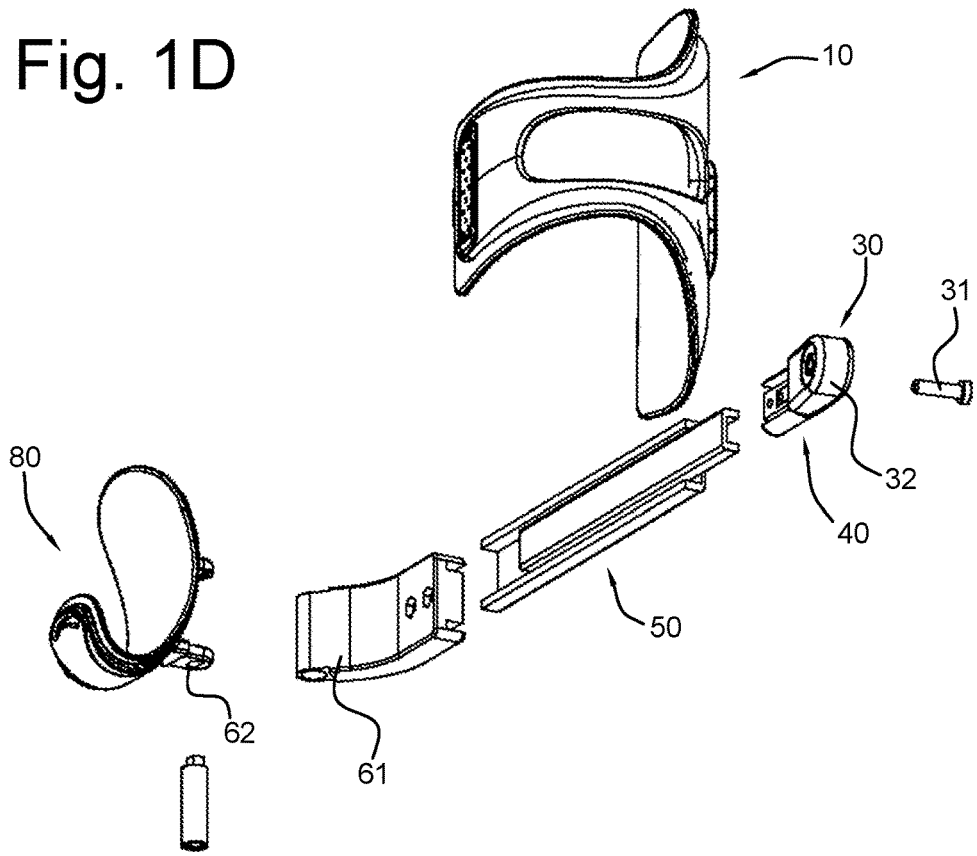

FIGS. 1C and 1D respectively show an exploded view of the same brace 1 and an exploded view form the back of the brace 1 and in which the straps have been omitted. The EFE joint 30, see also FIG. 1A, comprises a first portion 31 that for the right-handed use of the brace of FIGS. 1A-1D is fixed to the shell 11 at a first point of attachment 12a. The same brace can be configured for left-handed use by instead attaching the first portion 31 to the second point of attachment 12b, and by removing the second portion 62 of the WFE joint 60 from its first portion 61, turning over the second portion and hand piece 80 attached thereto, and then again reattaching the second portion to the first portion. This is possible, as both the upper arm piece 10, the hand piece 80, as well as the EFE, FPS and WFE joints are symmetrically shaped.

Thus, the same upper portion, EFE, FPS and WFE joint and the same extensible element 50 can be used for manufacturing a brace for left- or right-handed use, and optionally a brace that has been manufactured for right-handed use can be adapted for left-handed vice and vice versa.

As further shown in FIGS. 1C and 1D, the FPS joint 40 comprises a friction damper 43 arranged between the first portion 41 of the joint 40 to the second portion thereof. The damper 43 helps to reduce tremor as it substantially blocks rotation of the first portion 41 relative to the second portion if the torque between these portions is less than a predetermined threshold value.

The WFE joint 60 is provided with a liquid damper 63 arranged between the first portion 61 and second portion 62 of the WFE joint, and which dampens rotations at higher angular velocities of the first portion relative to the second portion around the third axis of rotation more than rotations at lower angular velocities.

Figure 2A:
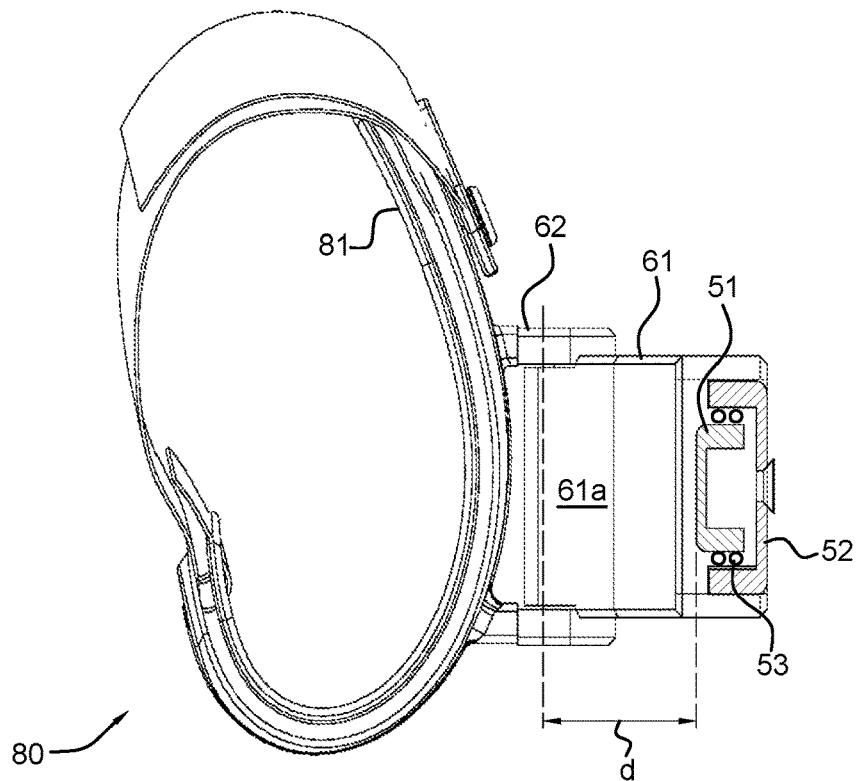

FIG. 2A shows a cross-sectional side view through plane P of FIG. 1B, which plane is normal to the longitudinal direction L, facing towards the hand piece 80. As can be seen the third axis of rotation R3 is spaced apart by a distance d from a closest part of the extension element 50, which in this case is the closest side of the first portion 51. Referring to FIGS. 1A-1C, it can be seen that the first part 61 of the WFE joint 60 has a concave inner side 61a which faces the user's wrist during use, and which curves from the second portion 52 towards the third axis of rotation R3. This allows a user to flex his or her hand without his or her wrist contacting the extension element 50. Roller bearings 53 between the first portion 51 and second portion 52 help ensure that the first portion can slide substantially freely relative to the second portion along the longitudinal direction of the extension element 50.

Figure 2B:
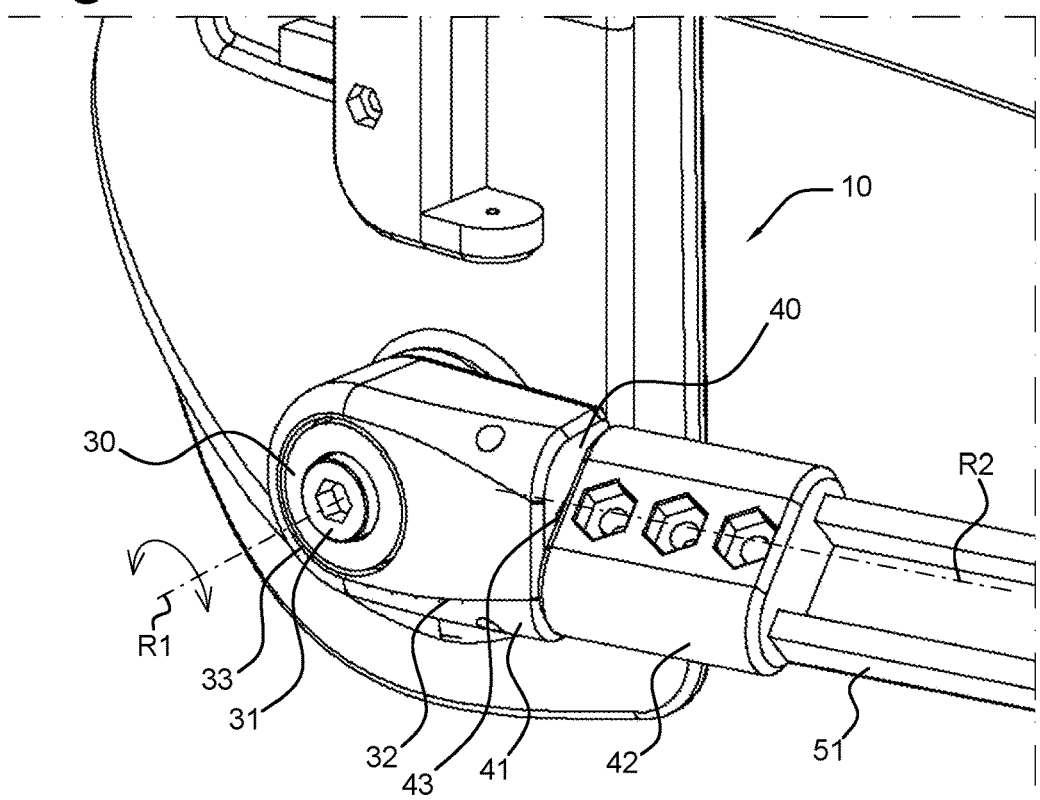

FIG. 2B shows a detail of the FPS joint 40 of FIG. 1A, but in a rotated position in which the second portion 42 has rotated over an angle of about 45 degrees about the second axis of rotation R2 relative to the first portion 41 of the joint, for allowing about 45 degrees pronation of the forearm.

Figure 3A:
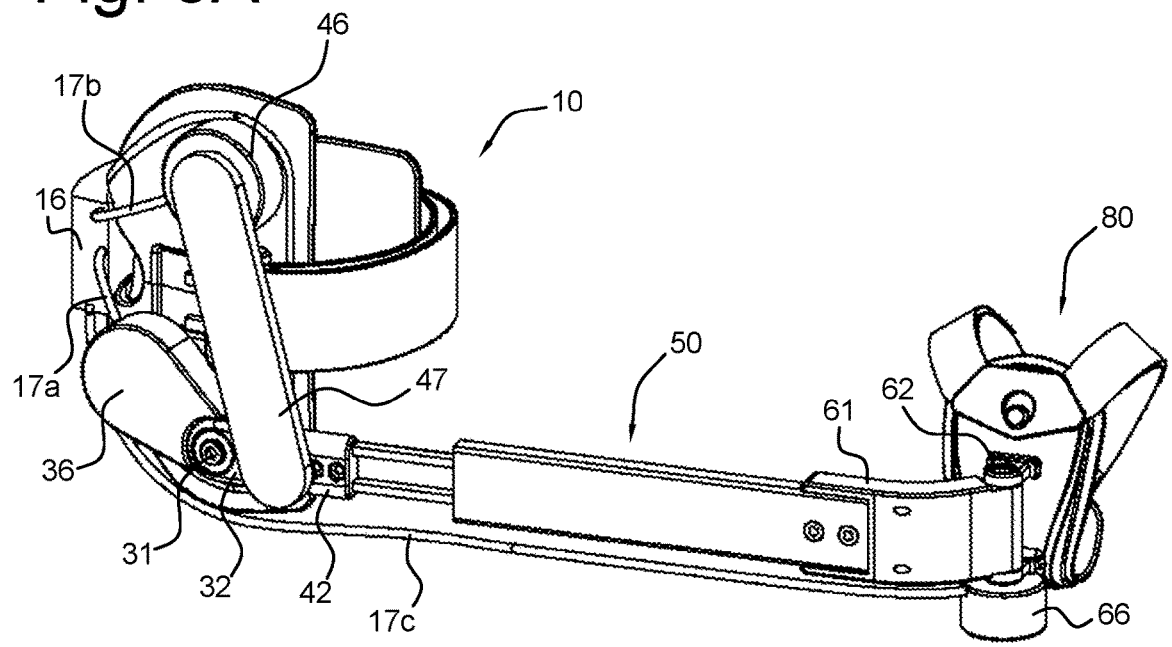
FIGS. 3A and 3B show examples of a brace according to the invention, provided respectively with actuators and sensors with which the brace may optionally be equipped.

FIG. 3A show a further embodiment of brace according to the invention, in which the brace is provided with actuators in the form of electromotors 36,46 and 66. Motor 36 is fixed to the upper shell of the arm piece 10 and arranged for driving rotation of the second portion 32 relative to the first portion 31 of the EFE joint around the first axis of rotation. The motor 36 is powered and controlled via conduit 17a which comprises conductors and is connected to control electronics 16. Rotation of the second portion 42 of the FPS joint relative to the first portion 41 thereof around the second axis of rotation can be driven by motor 46, which is also attached to the shell of the upper arm piece 10, and which transmits a force for driving said rotation through a transmission 47, here shown schematically. Motor 46 is powered and controlled via conduit 17b which comprises conductors and is also connected to the control electronics 16. A motor 66 is provided on the WFE joint, and is adapted for driving rotation of the first portion 61 of the WFE joint relative to the second portion 62 around the first axis of rotation. Motor 66 too is connected, via a conduit 17c comprising conductors, to the control electronics 16. A battery may be integrated in the control electronics for powering the motors 36, 46 and 66, though additionally or instead the control electronics 16 may be connected to an external battery.

The brace of FIG. 3A is suitable for generating movement of the user's elbow, forearm and wrist, and may for instance be used to simulate tremor, to control the motors to counteract tremor or to induce motion for rehabilitation.

Figure 3B:
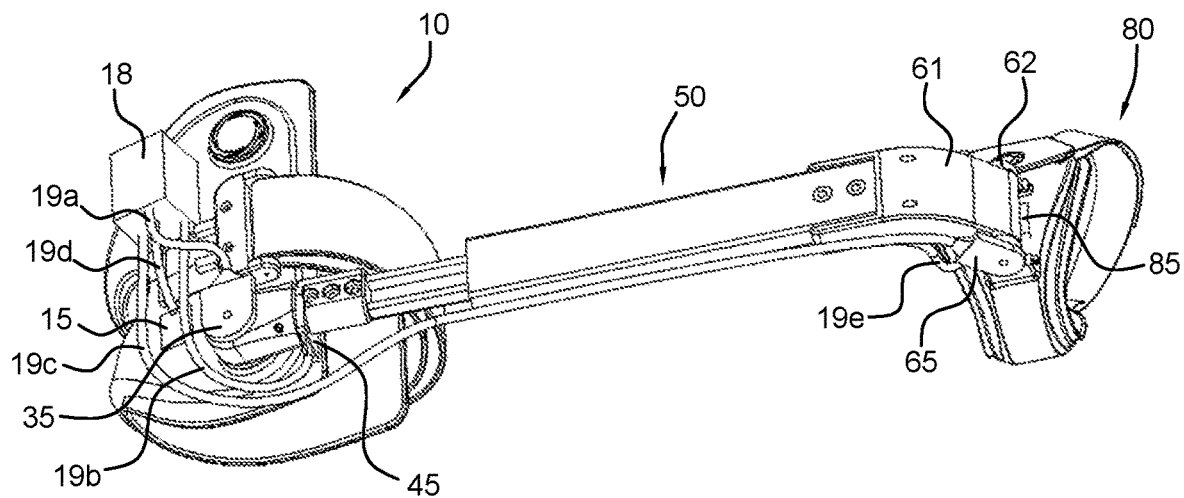

FIG. 3B shows an embodiment of a brace according to the invention, in which the brace is provided with sensors. In particular, the EFE joint is provided with a rotary encoder 35 for determining a rotational position of the first portion 31 of the EFE joint relative to the second portion 32 of the EFE joint around the first axis of rotation. The encoder is connected via conduit 19a to control electronics 18 that are adapted for receiving the sensor data, and optionally storing, transmitting and/or processing the sensor data. To measure a rotational position of the first portion 41 of the FPS joint relative to its second portion 42, the FPS joint is provided with a rotary encoder 45 which is connected to the control electronic vias conduit 19b. The WFE joint is provided with a rotary encoder 65, for determining a rotational position of the first portion 61 of the WFE joint relative to its second portion 62. The encoder 65 is connected via conduit 19c to the control electronics 18 Additionally, inertia measurement units 15 and 85 are provided respectively on the shell of the upper arm piece 10 and on the shell of the hand piece 80, and connected to the control electronics 18 via conduits 19d and 19e.

The sensors allow motion joints to be determined while a user is wearing the brace. It will be understood that when the embodiments of FIGS. 3A and 3B are combined, such that the brace is provided both with actuators and sensors, the control electronics 16 may be adapted for control the motors to counteract involuntary movement, based on data received from control electronics 17 which receives the sensor data.

Figure 4A:
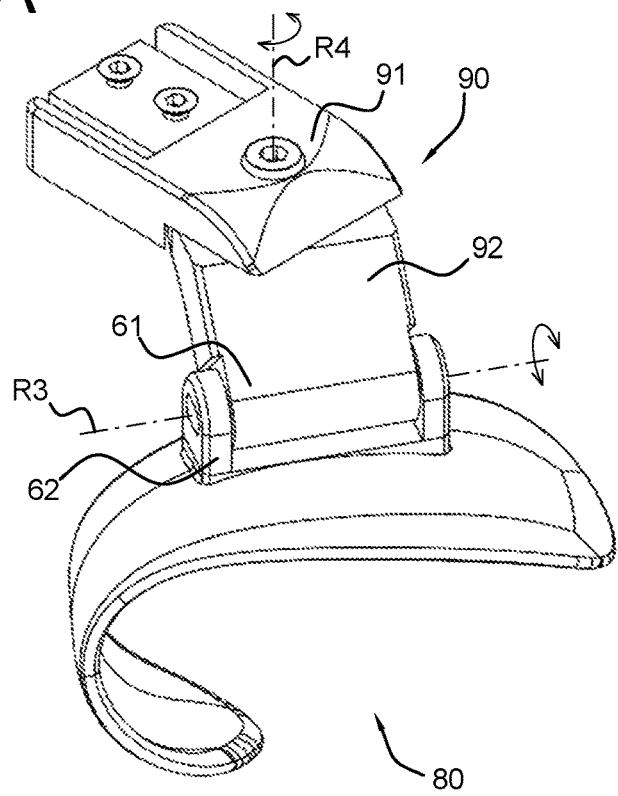
FIGS. 4A and 4B shows details of an alternative hand piece which is provided with a wrist adduction/abduction, WAA joint.
Figure 4B:
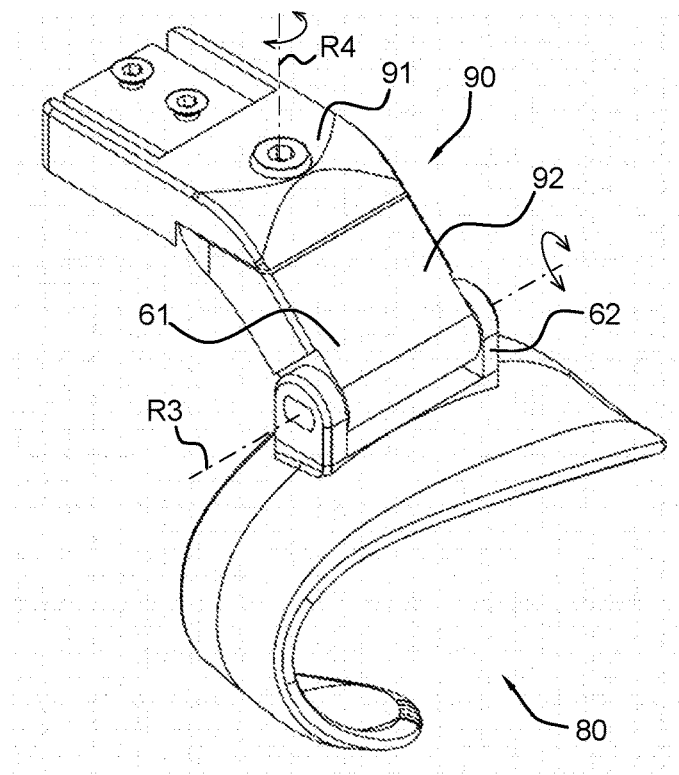

FIGS. 4A and 4B show a detail of a hand piece as may be used with the brace of FIG. 1A, wherein the brace further comprises a wrist adduction/abduction, WAA joint 90, having a first portion 91 and a second portion 92 which is rotatable relative to the first portion 91 around a fourth axis of rotation R4, to allow adduction or abduction of the user's wrist. The first portion is attached to the second end 52 of the extension element 50. The WAA joint may be provided with a damper, sensor and/or actuator. In this example the first portion 61 of the WFE joint 60 is indirectly connected to the second end of the extension element via the WAA joint 90 and the second portion of the WFE joint 60 is directly attached to the hand piece, i.e. is rotationally and translationally fixed with respect to the shell 81 of the handpiece 80.

FIGS. 5A and 5B show respectively an alternative hand piece 80' worn by a user, and a detail thereof. The hand piece 80', which may be used with the brace according to the invention instead of hand piece 80, comprises a substantially rigid shell 81' for supporting the ulnar side of the user's hand. Flexible strap 82' defines a first opening 01 through which the user can insert his or her thumb, and flexible strap 82' defines a second opening 02 through which the user can insert his or her fingers. The strap 83' may be fixedly attached to strap 82', or may be detachably attached thereto, e.g. using Velcro® or similar.

FIGS. 6A and 6B show an isometric view of a brace 100 according to an embodiment and an extension element as applied in the brace in a cutaway view, respectively.

The brace 100 according to the second embodiment is similar to the brace of the embodiment shown in FIG. 1A as brace 100 comprises an EFE joint 130, an FPS joint 140, an extension element 150, an WFE joint 160, and an upper arm piece 10 and a handpiece 80.

Similarly to what described above with reference to the embodiment described in FIGS. 1A-5B, the upper arm piece 10 is coupled to the EFE joint 130, the FPS joint 140, the extension element 150, the WFE joint 160 and the hand piece 80 to form a brace 100 between an upper arm of a person and the hand on that arm.

The FPS joint 140 comprises a first portion 141 which is integrated in the housing of the EFE joint 130 and a second portion 142 that is configured to rotate around the second axis of rotation R2 with respect to the first portion 141. The first portion 141 preferably comprises a rotational damper as described above with reference to the first embodiment.

In this embodiment the second portion 142 of the FPS joint 140 is integrated in the extension element 150, so as to allow the extension element to rotate along its longitudinal axis around the second axis of rotation R2.

Between the first portion 141 of the FPS joint 140 and the second portion 142 an axle 152 is extending along which the extension element 150 can be moved to allow user induced movement of the WFE joint relative to the FPS joint and EFE joint.

The axle 152 coincides with the longitudinal symmetry axis of the extension element 150 and provides a pivoting function to rotate the second portion 142 of the FPS joint relative to the first portion 141 around the second axis of rotation R2.

The extension element 150 comprises the axle 152 and a slider arrangement 154, 156, 157 comprising a pair of sliders 154 parallel to each other along the longitudinal direction L of the extension element 150, an entry linear bearing 157, and a sliding linear bearing 156, within a housing 155. The axle 152 is supported by the entry linear bearing 157 to guide the axle 152 within the housing 155. The entry linear bearing 157 is mounted in the housing 155 at an opening 158 where the axle 152 enters the housing 155.

An end 153 of the axle 152 inside the housing 155 is coupled to the sliding linear bearing 156 that is slideably connected to the pair of parallel sliders 154 so as to allow the end 153 of the axle to slide along the longitudinal direction of the extension element 150 and to allow to adjust the length of the extension element between the EFE joint 130 and the WFE joint 160.

In an embodiment, the first portion 141 of the FPS joint 140 comprises a rotational bearing 143 and is preferably configured with a rotational damper 144 to attenuate tremor-related rotations of the extension element due to forearm pronation-supination (FPS) rotation.

A collar 145 is arranged between the rotational bearing 143 and the rotational damper 144.

In an embodiment, the WFE joint 160 is configured with a releasable mount plate 162 that connects to the hand piece 80. The releasable mount plate 162 allows connecting to/disconnecting from the hand piece which allows a relatively easy fit of the brace 100 on a person's arm.

In a further embodiment, the WFE joint 160 is preferably configured with a damper (not shown) to attenuate tremor related movement of the handpiece 80 relative to the extension element 150.

FIG. 7 shows a cutaway view of an alternative mechanism for a wrist flexion-extension joint according to an embodiment.

The alternative mechanism 170 embodies a double joint 172 between the extension element 150 and the hand piece 80. The double joint 172 is arranged to couple the extension element and the hand piece such that the hand piece is moveable relative to the extension element.

The double joint comprises a housing 174, a first shaft 181, a second shaft 191, and first and second rotary joints 180, 190 that each can rotate around an axis 181; 191. The first and second shafts 181, 191 are mounted in the housing 174 parallel to each other at a predetermined distance from each other. The rotary joints 180; 190 are coupled to each other by meshed teeth on a pair of gearwheel segments 182; 192. It will be appreciated that alternative mechanical couplings between the rotary joints 180; 190 can be used as well for the purpose of coupled rotation of the rotary joints.

Optionally, each of the rotary joints 180, 190 is fitted with a respective damper 184, 194 of e.g. fluid, liquid or friction type. During use of the brace the dampers 184, 194 are configured to dampen undesirable motions of the handpiece 80 relative to the extension element 150.

The mechanism 170 prevents that the rotary joints rotate independently but only allow a linked movement of the joints 180, 190. Accordingly, the linked movement enables the extension element to stay close to the arm of a user while the user's wrist in the handpiece flexes and extends. Due to the coupling between the first and second joints, a rotation of the handpiece around the second joint 190 causes an additional rotation around the first joint in a same direction.

The hand piece 80 in this embodiment is configured to receive a dorsal side of a user's hand. The hand piece is attached to the hand by means of one or more straps (not shown) which can be connected to slots 195 in the hand piece 80.

In summary, the invention provides a body wearable brace, e.g. for resisting involuntary motion, adapted for allowing a user wearing the brace on his arm to dynamically move his or her upper arm, forearm, wrist and hand, comprising: an upper arm piece; a hand piece; an elbow flexion-extension joint comprising a first portion fixed to the upper arm piece and comprising a second portion that is rotatable relative to the upper arm piece around a first axis of rotation; a forearm pronation-supination joint comprising a first portion fixed to the second portion of the elbow flexion-extension joint, and a second portion that is rotatable relative to the first portion of the forearm pronation-supination joint and the second portion of the elbow flexion-extension joint around a second axis of rotation, to allow pronation and supination of the forearm; an extension element extending in a longitudinal direction and comprising a first portion and a second portion which is moveable relative to the first portion along the longitudinal direction, wherein the first portion of the extension element is fixed to the second portion of the forearm pronation-supination joint; a wrist flexion-extension joint comprising a first portion and a second portion that is rotatable relative to the first portion around a third axis of rotation, wherein the first portion of the wrist flexion-extension joint is directly or indirectly connected to the second portion of the extension element, and wherein the second portion of the wrist flexion-extension joint is directly or indirectly connected to the hand piece.

The present invention has been described above with reference to a number of exemplary embodiments as shown in the drawings. Modifications and alternative implementations of some parts or elements are possible, and are included in the scope of protection as defined in the appended claims.

The invention claimed is:

1. A body wearable brace adapted for allowing a user wearing the brace on his arm to dynamically move his or her upper arm, forearm, wrist and hand, comprising:
   an upper arm piece, for connecting the brace to the user's upper arm;
   a hand piece, for connecting the brace to the user's hand at least at a dorsal side thereof;
   an elbow flexion-extension ("EFE") joint, comprising an EFE joint first portion fixed to the upper arm piece and comprising an EFE joint second portion that is rotatable relative to the upper arm piece around a first axis of rotation, to allow flexion and extension of the elbow;
   a forearm pronation-supination ("FPS") joint, comprising an FPS joint first portion fixed to the second portion of the EFE joint, and an FPS joint second portion that is rotatable relative to the first portion of the FPS joint and the second portion of the EFE joint around a second axis of rotation, to allow pronation and supination of the forearm;
   wherein the brace further comprises:
   an extension element ("EE") extending in a longitudinal direction and comprising an EE first portion and an EE second portion which is moveable relative to the EE first portion along the longitudinal direction, wherein the first portion of the extension element is fixed to the second portion of the FPS joint;

a wrist flexion-extension, ("WFE") joint, comprising a WFE joint first portion and a WFE joint second portion that is rotatable relative to the WFE joint first portion around a third axis of rotation to allow flexion and extension of the wrist, wherein the first portion of the WFE joint is directly or indirectly connected to the second portion of the extension element, wherein the second portion of the WFE joint is directly or indirectly connected to the hand piece, and the brace is adapted for being completely spaced apart from the user's forearm during use, and wherein the brace is configured such that the forearm of the user is not encircled by the brace when in use.

2. The brace according to claim 1, wherein when seen in projection onto a plane normal to the longitudinal direction, the third axis of rotation is spaced apart from the first portion of the extension element by a distance of at least 0.7 cm.

3. The brace according to claim 1, wherein the first portion of the extension element is rotationally fixed to the second portion of the FPS joint, and wherein rotation of the second portion of the extension element around an axis parallel to its longitudinal direction relative to the first portion of the WFE joint is substantially blocked.

4. The brace according to claim 1, further comprising a wrist adduction-abduction ("WAA") joint, comprising a WWA joint first portion and a WA joint second portion that is rotatable relative to the WWA joint first portion around a fourth axis of rotation, wherein the WAA joint is connected between the hand piece and the second portion of the extension element to allow adduction and abduction of the user's wrist.

5. The brace according to claim 1, wherein the EFE joint, the WFE joint, the FPS joint and the WAA joint each comprise a motion resisting element adapted for resisting rotation of the first portions of the joints relative to the second portions of the joint, at a torque equal to or below a threshold.

6. The brace according to claim 1, wherein the EFE joint, the WFE joint, the FPS joint and the WAA joint each comprise a motion resisting element adapted for resisting fast rotation of the joints more than slower rotation of the joints.

7. The brace according to claim 1, wherein the EFE joint, the WFE joint, the FPS joint, the WAA joint and the extension element are provided with one of a fluid damper, a liquid damper and a friction damper for dampening movement of the first portions of the joints relative to the second portions of the joints.

8. The brace according to claim 1, wherein the WFE joint is a double joint comprising a pair of coupled joints.

9. The brace according to claim 1, wherein the first portion of the extension element is moveable relative to the second portion of the extension element along the longitudinal direction over a distance of at least 2 cm, the longitudinal direction is parallel with the second axis of rotation, and the extension element does not extend further along the longitudinal direction away from the FPS joint first portion than the WFE joint first portion.

10. The brace according to claim 1, wherein the brace is adapted for, when worn by the user, allowing substantially free pronation and supination of the user's forearm over a range of at least 90 degrees pronation to 90 degrees supination, and for allowing substantially free flexion and extension of the user's wrist over a range of at least 45 degrees flexion to 60 degrees extension.

11. The brace according to claim 1, wherein the extension element second member is substantially freely slidable relative to the extension element first member along the longitudinal direction.

12. The brace according to claim 1,
wherein the upper arm piece, the EFE joint, the FPS joint, the extension element, the WFE joint, the WAA joint and the hand piece are configurable to be used on a user's right arm and left arm; and
wherein the upper arm piece is provided with a first attachment element and with a second attachment element spaced apart from the first attachment element, wherein the first part of the EFE joint is attached the upper arm piece by means of either the first or the second attachment.

13. The brace according to claim 12, wherein one or more of the upper arm piece, the EFE joint, the FPS joint, the extension element, the WFE joint, the WAA joint and the hand piece have at least one plane of symmetry.

14. The brace according to claim 1,
wherein the upper arm piece comprises a shell adapted for, during use, being arranged at the triceps' side of the user's upper arm, and wherein the shell is configured to be open ended at the bicep's side of the user's upper arm to allow insertion of the user's upper arm from the open end;
wherein the upper arm piece is provided with an upper arm strap adapted for placement around a portion of the user's arm above the crook of the arm and below or at a lower side of the user's biceps, and for connecting to the shell; and
wherein the upper arm piece comprises a magnetic clasp for holding a portion of the upper arm strap in place with respect to the shell.

15. The brace according to claim 1, wherein the hand piece comprises one of
a shell with a substantially rigid portion adapted for supporting the ulnar side and dorsal side of the user's hand during use while being spaced apart from the radial side of the user's hand; and
a shell with a substantially rigid portion adapted for supporting the dorsal side of the user's hand during use while being spaced apart from the ulnar and radial side of the user's hand.

16. The brace according to claim 1, wherein the hand piece comprises a shell adapted with a substantially rigid portion for supporting the radial side and dorsal side of the user's hand during use while being spaced apart from the ulnar side of the user's hand.

17. The brace according to claim 15,
wherein the hand piece is provided with one or more straps respectively for placement around the user's wrist or palm and connecting to the rigid portion of the shell of the hand piece;
wherein the hand piece comprises one or more magnetic clasps for holding a portion of the one or more straps in place with respect to the substantially rigid shell of the hand piece; and
wherein the rigid shell of the hand piece comprises a deformable metal sheet, for allowing the shape of the hand piece to be adjusted to the user's hand.

18. The brace according to claim 1, wherein the brace is completely passive.

19. The brace according to claim 1,
wherein the brace is provided with one or more sensors for sensing a relative position of one part of the brace to another part of the brace, and torque applied between one part of the brace and another part of the brace;

wherein the EFE joint, the FPS joint, WAA joint, the extension element, and the WFE joint are provided with an actuator for urging the first part and the second part of the joint to an adjustable position; and wherein the EFE joint, the FPS joint, the WAA joint, the extension element, and the WFE joint are provided with an actuator for restricting involuntary motion while allowing and/or supporting voluntary motion.

20. A body wearable brace adapted for allowing a user wearing the brace on his arm to dynamically move his or her upper arm, forearm, wrist and hand, comprising:

an upper arm piece, for connecting the brace to the user's upper arm;

a hand piece, for connecting the brace to the user's hand at least at a dorsal side thereof;

an elbow flexion-extension ("EFE") joint, comprising an EFE joint first portion fixed to the upper arm piece and comprising an EFE joint second portion that is rotatable relative to the upper arm piece around a first axis of rotation, to allow flexion and extension of the elbow;

a forearm pronation-supination ("FPS") joint, comprising an FPS joint first portion fixed to the second portion of the EFE joint, and an FPS joint second portion that is rotatable relative to the first portion of the FPS joint and the second portion of the EFE joint around a second axis of rotation, to allow pronation and supination of the forearm;

wherein the brace further comprises an extension element ("EE") extending in a longitudinal direction and comprising an EE first portion and an EE second portion which is moveable relative to the EE first portion along the longitudinal direction, wherein the first portion of the extension element is fixed to the second portion of the FPS joint;

a wrist flexion-extension ("WFE") joint, comprising a WFE joint first portion and a WFE joint second portion that is rotatable relative to the WFE joint first portion around a third axis of rotation to allow flexion and extension of the wrist, wherein the first portion of the WFE joint is directly or indirectly connected to the second portion of the extension element, and wherein the second portion of the WFE joint is directly or indirectly connected to the hand piece, the brace is adapted for being completely spaced apart from the user's forearm during use;

the second axis of rotation is configured to be spaced from users body when brace is in use;

the EFE joint second portion intersects with the second axis of rotation;

no portion of the extension element crosses the surface of a further plane, wherein the third axis and the intersection of the first axis and the second axis lie on the surface of the further plane;

the intersection of the first axis and the second axis adjacent to but exterior to a space encircled by the upper arm piece when the upper arm strap is engaged;

the brace is configured to only contact the user's body at the upper arm piece and the hand piece when the brace is in use; and the brace is configured to not contact the user's body between the upper arm piece and the hand piece when the brace is in use.

* * * * *